(12) United States Patent
Benitez et al.

(10) Patent No.: US 9,663,430 B2
(45) Date of Patent: May 30, 2017

(54) PROCESS FOR MAKING PHENOL AND/OR CYCLOHEXANONE

(71) Applicant: ExxonMobil Chemical Patents Inc., Baytown, TX (US)

(72) Inventors: Francisco M. Benitez, Cypress, TX (US); Christopher L. Becker, Manhattan, KS (US); Keith H. Kuechler, Friendswood, TX (US); Jason D. Davis, Beaumont, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/912,569

(22) PCT Filed: Aug. 27, 2014

(86) PCT No.: PCT/US2014/052891
§ 371 (c)(1),
(2) Date: Feb. 17, 2016

(87) PCT Pub. No.: WO2015/050649
PCT Pub. Date: Apr. 9, 2015

(65) Prior Publication Data
US 2016/0251288 A1    Sep. 1, 2016

Related U.S. Application Data

(60) Provisional application No. 61/885,077, filed on Oct. 1, 2013.

(30) Foreign Application Priority Data

Jan. 16, 2014  (EP) .................................... 14151423

(51) Int. Cl.
*C07C 45/53* (2006.01)
*C07C 37/08* (2006.01)
*C07C 2/74* (2006.01)
*C07C 407/00* (2006.01)
*C07C 45/00* (2006.01)

(52) U.S. Cl.
CPC .............. *C07C 37/08* (2013.01); *C07C 45/00* (2013.01); *C07C 45/53* (2013.01); *C07C 407/00* (2013.01); *C07C 407/003* (2013.01); *C07C 2101/14* (2013.01)

(58) Field of Classification Search
CPC   C07C 45/53; C07C 37/08; C07C 2/74; C07C 407/00
USPC .................. 568/342, 347, 570, 798; 585/467
See application file for complete search history.

(56) References Cited

U.S. PATENT DOCUMENTS 6,037,513 A    3/2000 Chang et al.

FOREIGN PATENT DOCUMENTS

| WO | 00/12470 | 3/2000 |
| WO | 2010/042273 | 4/2010 |
| WO | 2012/036822 | 3/2012 |
| WO | 2012/134549 | 10/2012 |
| WO | 2013/119407 | 8/2013 |
| WO | 2014/137623 | 9/2014 |

*Primary Examiner* — Sikarl Witherspoon

(57) ABSTRACT

A process for making phenol and/or cyclohexanone, the process comprising: (A) oxidizing a cyclohexylbenzene feed to obtain an oxidation product comprising cyclohexylbenzene, cyclohexylbenzene hydroperoxide and water; (B) removing at least a portion of the water from at least a portion of the oxidation product to obtain a cleavage feed; and (C) contacting at least a portion of the cyclohexylbenzene hydroperoxide in the cleavage feed with an acid catalyst in a cleavage reactor under cleavage conditions to obtain a cleavage product comprising phenol and cyclohexanone. The removing step may also comprises a step of removing a portion of the cyclohexylbenzene contained in the oxidation product. Water removal may be advantageously conducted in a water flashing drum before a cyclohexylbenzene hydroperoxide concentrator.

20 Claims, No Drawings

PROCESS FOR MAKING PHENOL AND/OR CYCLOHEXANONE

PRIORITY CLAIM

This application claims priority to U.S. Provisional Application Ser. No. 61/885,077 filed Oct. 1, 2013, and European Application No. 14151423.2 filed Jan. 16, 2014, the disclosures of which are fully incorporated herein by their reference.

FIELD

The present invention relates to a process for making phenol and/or cyclohexanone. In particular, the present invention relates to a process for making phenol and/or cyclohexanone by the cleavage of cyclohexylbenzene hydroperoxide. The present invention is useful, e.g., in making phenol and cyclohexanone via the route of benzene hydroalkylation.

BACKGROUND

Phenol and cyclohexanone are important materials in the chemical industry and are useful in, for example, the production of phenolic resins, bisphenol A, ε-caprolactam, adipic acid, and plasticizers.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. However, the world demand for phenol is growing more rapidly than that for acetone. In addition, the cost of propylene feed is generally high.

Thus, a process that uses higher alkenes instead of propylene as feed and coproduces higher ketones, such as cyclohexanone, rather than acetone may be an attractive alternative route to the production of phenols. There is also a growing demand for cyclohexanone.

It is known from, e.g., U.S. Pat. No. 6,037,513 that cyclohexylbenzene can be produced by contacting benzene with hydrogen in the presence of a bifunctional catalyst comprising a molecular sieve of the MCM-22 type and at least one hydrogenation metal selected from palladium, ruthenium, nickel, cobalt, and mixtures thereof. This reference also discloses that the resultant cyclohexylbenzene can be oxidized to the corresponding hydroperoxide which is then decomposed to the desired phenol and cyclohexanone co-product.

The oxidation of cyclohexylbenzene to produce cyclohexylbenzene hydroperoxide and the cleavage of cyclohexylbenzene hydroperoxide to produce phenol and cyclohexanone are much more complex than the cumene oxidation and cumene hydroperoxide cleavage in the Hock process. Many process parameters can affect the final yield of phenol and cyclohexanone in the cyclohexylbenzene hydroperoxide cleavage step.

SUMMARY

It has been found that in the cyclohexylbenzene oxidation product, water is present at a non-negligible amount and the residual cyclohexylbenzene concentration may be high. It has also been found that the presence of water in the cleavage feed can slow the reaction rate of the cyclohexylbenzene hydroperoxide cleavage reaction, and that the presence of cyclohexylbenzene at a high concentration in the cleavage reaction media can reduce the selectivity of phenol and/or cyclohexanone. The method of the present disclosure, by reducing water and/or cyclohexylbenzene concentration(s) in the cleavage feed, increases the overall yield(s) of phenol and/or cyclohexanone.

The present disclosure relates to a process for making phenol and/or cyclohexanone, the process comprising:
 (A) oxidizing a cyclohexylbenzene feed to obtain an oxidation product comprising cyclohexylbenzene, cyclohexylbenzene hydroperoxide and water;
 (B) removing at least a portion of the water from at least a portion of the oxidation product to obtain a cleavage feed; and
 (C) contacting at least a portion of the cyclohexylbenzene hydroperoxide in the cleavage feed with an acid catalyst in a cleavage reactor under cleavage conditions to obtain a cleavage product comprising phenol and cyclohexanone.

Step (B) may comprise (B1) flashing the oxidation product at an absolute pressure of at most 50 kPa. Alternatively, step (B) may comprise: (B2) separating at least a portion of the cyclohexylbenzene from the oxidation product. Alternatively, step (B) may comprise both (B1) and (B2) above, and the steps (B1) and (B2) may be conducted in separate vessels or in the same vessel.

DETAILED DESCRIPTION

In the present disclosure, a process is described as comprising at least one "step." It should be understood that each step is an action or operation that may be conducted once or multiple times in the process, in a continuous or discontinuous fashion. Unless specified to the contrary or the context clearly indicates otherwise, each step in a process may be conducted sequentially in the order as they are listed, with or without overlapping with one or more other step(s), or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be conducted simultaneously with respect to an intermediate material resulting from treating the raw materials fed into the process at an earlier time in the first step. Preferably, however, steps are performed in the order specified.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenation metal" include embodiments where one, two or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question unless specified or indicated otherwise. All ranges expressed herein should include both end points as two specific embodiments unless specified or indicated to the contrary.

As used herein, the generic term "dicylcohexylbenzene" includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in singular form, means mono substituted cyclohexylbenzene.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Non-limiting examples of materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITQ-2.

Supply of Cyclohexylbenzene

The cyclohexylbenzene supplied to step (A) of the process of the present disclosure can be supplied by chemical reactions of certain raw materials, such as those described below (e.g., a hydroalkylation reaction), or by recycling of residual cyclohexylbenzene not consumed in subsequent process steps where a cyclohexylbenzene-containing feed is subjected to a chemical reaction, such as oxidation.

In the integrated process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 type molecular sieve, or by oxidative coupling of benzene to make biphenyl followed by hydrogenation of the biphenyl. However, in practice, the cyclohexylbenzene is desirably produced by contacting the benzene with hydrogen under hydroalkylation conditions in the presence of a hydroalkylation catalyst whereby the benzene undergoes the following Reaction-1 to produce cyclohexylbenzene (CHB):

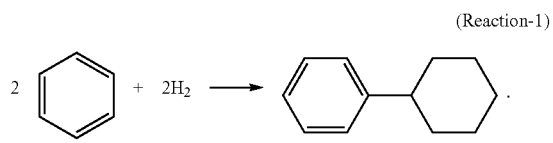 [SMILES: c1ccccc1 ; c1ccc(C2CCCCC2)cc1]

(Reaction-1)

U.S. Pat. Nos. 6,730,625 and 7,579,511; WO2009/131769; and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include palladium, ruthenium, nickel, zinc, tin, and cobalt, with palladium being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, $SnO$, $SnO_2$, and mixtures, combinations and complexes thereof.

Although the hydroalkylation reaction is highly selective towards cyclohexylbenzene, the effluent from the hydroalkylation reaction may contain some dialkylated products, unreacted benzene and cyclohexane. The unreacted benzene may be recovered by distillation and recycled to the reactor. The lower effluent from the benzene distillation may be further distilled to separate the monocyclohexylbenzene product from dicyclohexylbenzene and other heavies. Depending on the quantity of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partial liquid phase conditions, which suitably include a temperature of 100° C. to 300° C., a pressure of 800 kPa to 3500 kPa, a weight hourly space velocity of 1 hr$^{-1}$ to 10 hr$^{-1}$ on total feed, and a benzene/dicyclohexylbenzene weight ratio of 1:1 to 5:1.

Oxidation of Cyclohexylbenzene

Depending on the production method or source, the cyclohexylbenzene supplied to step (A) can contain a certain concentration of water, e.g., in a range from A1 ppm to A2 ppm by weight, based on the total weight of the cyclohexylbenzene feed supplied to the oxidation reactor, where A1 and A2 can be, independently, 5, 10, 20, 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as A1<A2. For example, cyclohexylbenzene separated from the reaction product of a subsequent reaction step, such as oxidation and cleavage described in detailed below, may be subjected to treatment such as washing and/or purification using a water-containing media (such as an aqueous dispersion) before recycled and supplied to step (A), and therefore contains water at a relatively high concentration, such as in a range from A1 ppm and A2 ppm by weight, where A1 and A2 are described above, and A1≥500.

After removal of the unreacted benzene and the polyalkylated benzenes and other heavy species, the cyclohexylbenzene is fed to the oxidizing step (A), which can be conducted in one or more oxidation reactor(s). Desirably, at least a portion of the cyclohexylbenzene contained in the oxidation feed is converted to cyclohexyl-1-phenyl-1-hydroperoxide, the desired hydroperoxide according to the following Reaction-2:

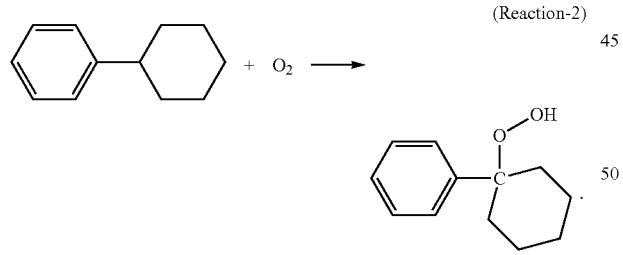

(Reaction-2)

A feed supplied to the oxidizing step (A) may comprise cyclohexylbenzene at a concentration in a range from C1 wt % to C2 wt %, based on the total weight of the feed introduced into the oxidation reactor, where C1 and C2 can be, independently, 10, 20, 30, 40, 50, 60, 70, 80, 90, 92, 94, 95, 96, 97, 98, 99, 99.5, or even 99.9, or even higher, as long as C1<C2. In addition, the feed to the oxidizing step (A) may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) phenylmethylcyclopentane, including one or more of 1-phenyl-1-methylcyclopentane, 1-phenyl-2-methylcyclopentane, and 1-phenyl-3-methylcyclopentane, at a total concentration in a range from 1 ppm to 2 wt %, such as from 10 ppm to 1 wt %; (iv) phenol at a concentration no greater than 1000 ppm, such as no greater than 100 ppm; and (v) olefins or alkene benzenes such as phenylcyclohexene at no greater than 1000 ppm.

The oxidizing step (A) may be accomplished by contacting an oxygen-containing gas, such as air and various derivatives of air, with the feed comprising cyclohexylbenzene. A stream of $O_2$, pure air, or other $O_2$-containing mixtures may be pumped through the cyclohexylbenzene-containing feed in an oxidation reactor such as a bubble column to effect the oxidation.

The oxidation may be conducted in the absence or presence of a catalyst. Examples of suitable oxidation catalysts include those having a structure of formula (FC-I), (FC-II), or (FC-III) below:

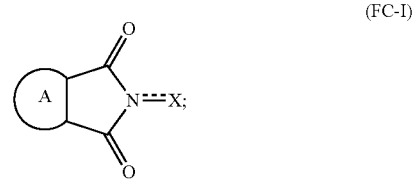

(FC-I)

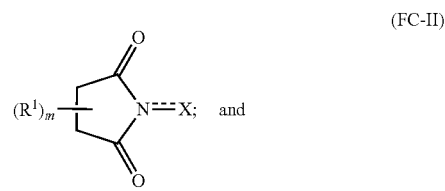

(FC-II)

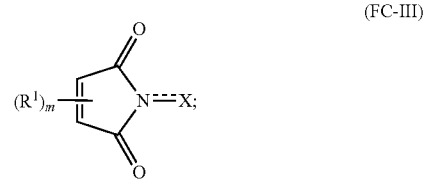

(FC-III)

where:

A represents a ring optionally comprising a nitrogen, sulfur, or oxygen in the ring structure, and optionally substituted by an alkyl group, an alkenyl group, a halogen, or a N-, S-, or O-containing group or other group;

X represents a hydrogen, an oxygen, a hydroxyl group, or a halogen;

$R^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl group, an alkenyl, a halogen, or a N-, S-, or O-containing group or other group; and m is 0, 1 or 2.

Examples of particularly suitable catalysts for the oxidation step (A) include those represented by the following formula (FC-IV):

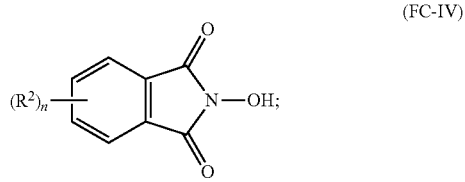

where:

R², the same or different at each occurrence, independently represents a halogen, a N-, S-, or O-containing group, or linear or branched acyclic alkyl or cyclic alkyl group having 1 to 20 carbon atoms optionally substituted by an alkyl group, an alkenyl group, a halogen, or a N-, S-, or O-containing group or other group; and n is 0, 1, 2, 3, or 4.

Especially suitable catalyst having the above formula (FC-IV) for the oxidation step (A) is NHPI (N-hydroxy phthalic imide).

Non-limiting examples of suitable reaction conditions of the oxidizing step (A) include a temperature from 70° C. to 200° C., such as 90° C. to 130° C., and a pressure of 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step (A) may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series, each operating at the same or different conditions selected to enhance the oxidation reaction of reaction media with different compositions. The oxidation reactor may be operated in a batch, semi-batch, or continuous flow manner well known to those skilled in the art.

Treatment of the Oxidation Product before Cleavage

Desirably, the oxidation product exiting the oxidation reactor contains cyclohexyl-1-phenyl-1-hydroperoxide at a concentration in a range from Chp1 wt % to Chp2 wt %, based on the total weight of the oxidation product, where Chp1 and Chp2 can be, independently, 5, 10, 15, 20, 25, 30, 35, 40, 45, 50, 55, 60, 65, 70, 75, 80, as long as Chp1<Chp2. The oxidation product may further comprise (i) an oxidation catalyst described above; and (ii) unreacted cyclohexylbenzene at a concentration in a range from Cchb1 wt % to Cchb2 wt %, based on the total weight of the oxidation product, where Cchb1 and Cchb2 can be, independently, 20, 25, 30, 35, 40, 45, 50, 55, 60, 65, 70, 75, 80, 85, 90, 95, as long as Cchb1<Cchb2.

In addition, the oxidation product may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in feed supplied to step (A), such as cyclohexyl-2-phenyl-1-hydroperoxide, and cyclohexyl-3-phenyl-1-hydroperoxide. These undesired hydroperoxides are desirably at a total concentration of at most 5 wt %, such as at most 3 wt %, 2 wt %, 1 wt %, or even 0.1 wt %. They are undesirable because they may not convert into phenol and cyclohexanone in the cleavage reaction at the desired conversion and/or selectivity, resulting in overall yield loss.

The oxidation product invariably contains water because: (i) as mentioned above, depending on the production method and source, the cyclohexylbenzene fed to step (A) can contain water at a certain level; and (ii) during the oxidation reaction, water is produced due to, inter alia, premature decomposition of the hydroperoxides produced. While a portion of the water contained in the reaction media in step (A) can be carried away if a stream of gas passes through the oxidation reaction medium and exits the oxidation reactor, some water will remain in the oxidation product. The concentration of water in the oxidation product exiting the oxidation reactor is C1 ppm by weight, based on the total weight of the oxidation product, which can range from C1a ppm to C1b ppm, where C1a and C1b can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as C1a<C1b.

The oxidation product contains the oxidation catalyst, such as NHPI, and certain by-products. Thus, it may be desirable to wash the oxidation product to remove the by-products and/or the catalyst before cleavage by using an aqueous dispersion. For example, a basic aqueous dispersion, such as a solution of one or more of alkali or alkali earth carbonates, alkali or alkali earth bicarbonates, alkali or alkali earth hydroxides, ammonium hydroxide, may be used to wash the oxidation product to extract NHPI or other similar imide-based catalysts from the oxidation product. In so doing, water concentration in the oxidation product thus washed will increase.

Alternatively, to reclaim the oxidation catalyst from the oxidation product, the oxidation product may be subject to contacting with a solid sorbent, in the form of particles in a slurry or a fixed bed, such as solid alkali or alkali earth metal carbonates, alkali or alkali earth metal bicarbonates, alkali or alkali earth metal hydroxide, molecular sieves, activated carbon, and the like. After separation, the sorbent may be washed using a polar solvent, such as water, acetone, an alcohol, and the like, to reclaim the oxidation catalyst, which can be purified and recycled to the oxidation reactor.

In the process of the present disclosure, at least a portion of the cyclohexylbenzene hydroperoxide in the oxidation product is subjected to a cleavage reaction, desirably in the presence of a catalyst such as an acid, whereby it is converted into phenol and/or cyclohexanone.

It has been found that the water contained in the optionally treated oxidation product, if not reduced and fed into the cleavage step in the cleavage feed in its entirety, can be detrimental to the cleavage step. Without intending to be bound by a particular theory, it is believed that water in the cleavage feed can slow down the reaction rate of the cleavage reaction to an undesirable level. In addition, in cleavage reactions catalyzed by a liquid acid, such as sulfuric acid, the presence of water in the reaction medium can lead to the corrosion of the reactor equipment. As such, it is desired that water is at least partly removed from the oxidation product before the cleavage reaction.

In exemplary embodiments, at least a portion of the oxidation product is fed into the cleavage reactor without substantial alteration of the concentration of cyclohexylbenzene hydroperoxide and/or cyclohexylbenzene therein. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, in these embodiments, the following relationship may be satisfied: $(CCHB(op)-CCHB(cf))/CCHB(cf))\leq 0.05$. In these embodiments, the oxidation product may be flashed in a vessel at an absolute pressure in a range from Pf1 kPa to Pf2 kPa to remove a portion of water contained therein, where Pf1 and Pf2 can be, independently, 2.50, 2.67, 3.00, 3.50, 4.00, 4.50, 5.00, 5.50, 6.00, 6.50, 6.67, 7.00, 7.50, 8.00, 8.50, 9.00, 10.00, 11.00, 12.00, 13.00, 13.33, 14.00, 15.00, 16.00, 17.00, 18.00, 19.00, 20.00, 25.00, 30.00, 35.00, 40.00, 45.00, or 50.00, as long as Pf1<Pf2. Advantageously, the oxidation product is flashed in a vessel, such as a flashing drum, at an absolute pressure in a range from 6.67 kPa (50 torr) to 13.33 kPa (100 torr). The low absolute pressure inside the vessel can be imparted by a vacuum pump, such as a liquid ring vacuum pump using chilled water (e.g., water at 15° C.) or oil (such as cyclohexylbenzene) as the ring liquid. During the flashing step, other low boiling components that may be present in the oxidation product, such as lower acids (e.g., formic acid, acetic acid, and the like) and low boiling point hydrocarbons (e.g., benzene, cyclohexane, methylcyclopentane, and the like), may be at least partially removed along with water, resulting in a cleaner cleavage feed.

Alternatively and desirably, at least a portion of the oxidation product is not fed into the cleavage reactor before the concentration of cyclohexylbenzene therein is significantly reduced, and hence, the concentration of cyclohexylbenzene hydroperoxide therein is significantly increased. Thus, where the concentration of cyclohexylbenzene in the oxidation product is CCHB(op) wt % based on the total weight of the oxidation product, and the concentration of cyclohexylbenzene in the cleavage feed is CCHB(cf) wt % based on the total weight of the cleavage feed before any material other than those contained in the oxidation product is added, in these embodiments, the following relationship may be satisfied: $R1<(CCHB(op)-CCHB(cf))/CCHB(op))\leq R2$, where R1 and R2 are, independently, 0.05, 0.08, 0.10, 0.12, 0.14, 0.15, 0.18, 0.20, 0.25, 0.30, 0.35, 0.40, 0.45, 0.50, 0.55, 0.60, 0.70, 0.75, 0.80, 0.85, or even 0.90, as long as R1<R2. Advantageously, R1=0.25, and R2=0.75. The reduction of cyclohexylbenzene concentration from the oxidation product before cleavage is particularly advantageous where liquid acid, such as sulfuric acid, is used as the cleavage catalyst. Without intending to be bound by a particular theory, it is believed that this is because the liquid acid tends to have low solubility in cyclohexylbenzene, and the desired catalytic effect of the liquid acid can be significantly reduced as a result of high cyclohexylbenzene concentration. Experimental data have shown that partial removal of cyclohexylbenzene concentration from the oxidation product before it is fed to the cleavage step can significantly improve the selectivity of the cleavage reaction to form the desired products, i.e., cyclohexanone and/or phenol.

Because cyclohexylbenzene hydroperoxide is prone to decomposition at an elevated temperature, e.g., at above 150° C., the removal of cyclohexylbenzene from the oxidation product should generally be conducted at a relatively low temperature, e.g., no higher than 150° C., or no higher than 140° C., or no higher than 130° C., or no higher than 120° C., or even no higher than 110° C. Cyclohexylbenzene has a high boiling point (239° C. at 101 kPa). Thus, at the acceptable cyclohexylbenzene-removal temperature, cyclohexylbenzene tends to have very low vapor pressure. Accordingly, desirably, to effectively remove a meaningful amount of cyclohexylbenzene from the oxidation product, the oxidation product is subjected to a very low absolute pressure, e.g., in a range from Pc1 kPa to Pc2 kPa, where Pc1 and Pc2 can be, independently, 0.13, 0.15, 0.20, 0.25, 0.26, 0.30, 0.35, 0.39, 0.40, 0.45, 0.50, 0.60, 0.65, 0.70, 0.75, 0.80, 0.85, 0.90, 0.95, 1.00, 1.33, 1.50, 2.00, 2.50, 2.66, as long as Pc1<Pc2. Particularly advantageously, Pc1=0.27, and Pc2=2.00.

Where cyclohexylbenzene is partly removed from the oxidation product before cleavage, water contained in the oxidation product can be at least partly removed at the same time and in the same vessel where the cyclohexylbenzene is partly removed at a low absolute internal pressure. Indeed, if water contained in the oxidation product was not partly removed before the step of removing cyclohexylbenzene, water would likely be substantially completely removed from the oxidation product when cyclohexylbenzene is partly removed due to the temperature and low pressure applied. Where the oxidation product comprises water at a relatively low concentration, such as below 100 ppm by weight, or below 50 ppm, or even below 30 ppm, based on the total weight of the oxidation product, the oxidation product may be fed into a single vessel operating at the very low pressure where water and a portion of the cyclohexylbenzene are removed simultaneously.

Because of the very low absolute pressure required for effective cyclohexylbenzene removal, it is highly desired that before the oxidation product is subjected to cyclohexylbenzene removal, components with boiling points substantially lower than cyclohexylbenzene, such as water, benzene, cyclohexane, lower acids, and the like, contained in the oxidation product are removed at a relatively high pressure before the mixture is subjected to the very low pressure required for cyclohexylbenzene removal, such that the vacuum pump used for imparting the very low pressure is not overwhelmed. To that end, the oxidation product, upon exiting the oxidation reactor, may be first flashed in a first vessel such as a flashing drum at an absolute pressure in a range from Pf1 kPa to Pf2 kPa, where Pf1 and Pf2 can be, independently, 2.67, 3.00, 3.50, 4.00, 4.50, 5.00, 6.00, 7.00, 8.00, 9.00, 10.00, 11.00, 12.00, 13.00, 13.33, 14.00, 15.00, 20.00, 25.00, 30.00, 35.00, 40.00, 45.00, 50,00, as long as Pf1<Pf2, where a majority of the water contained in the oxidation product is removed, and desirably less than AA % of the cyclohexylbenzene contained in the oxidation product is removed, the percentage based on the total amount of cyclohexylbenzene contained in the oxidation product, where AA can be: 5, 4, 3, 2, 1, 0.8, 0.6, 0.5, 0.4, 0.3, 0.2, or 0.1.

Removal of cyclohexylbenzene from the oxidation product can be advantageously conducted in a concentrator comprising one or more falling film evaporator(s), such as those described in co-pending, co-assigned U.S. Provisional Patent Application Ser. No. 61/841,072 filed on Jun. 28, 2013 and entitled "Process for Concentrating a Mixture Containing Organic Hydroperoxide." The concentrator advantageously employs one or more falling film evaporators operating in parallel and/or in series operating under very low absolute pressure(s) described above. Because cyclohexylbenzene has a lower boiling point than cyclohexylbenzene hydroperoxide, a portion of the cyclohexylbenzene contained in the oxidation product evaporates under the very low pressure and is enriched in the vapor phase, condensed and collected for recycling back to the oxidizing step (A). Since by-products produced in the oxidizing step (A) tend to accumulate in the condensed cyclohexylbenzene stream, a washing or extracting treatment of the condensed cyclohexylbenzene using an aqueous dispersion or other agent may be desired before the recycling thereof to the oxidizing step (A) in order to prevent interference of the oxidation reaction of cyclohexylbenzene by the accumulated oxidation by-products. Such aqueous dispersion may be acidic, basic, or neutral in pH. The washing or extracting treatment may advantageously include a first step of chemical wash followed by a step of washing using water only. The thus washed reclaimed cyclohexylbenzene may be dried by using a water sorbent, such as a 3 Å molecular sieve before being recycled to step (A). Alternatively, because water up to a certain amount is tolerated in the oxidation reactor, the thus washed cyclohexylbenzene, which contains a significant amount of water, may be fed to the oxidizing step (A) directly without drying as at least a portion of the total feed, thus eliminating the cost of drying.

As an alternative approach, water removal of the optionally treated oxidation product can be effected by passing the liquid mixture through a water sorbent, such as a 3 Å molecular sieve. Advantageously, the water sorbent also adsorbs the oxidation catalyst, which may be reclaimed by washing with a polar solvent.

Additionally or alternatively, after water removal and before or after partial cyclohexylbenzene removal, all or a portion of the oxidation product may be cooled to cause crystallization of the unreacted imide oxidation catalyst, which may then be separated either by filtration or by scraping from a heat exchanger surface used to effect the crystallization.

Cleavage Reaction

As discussed above, the process includes cleaving at least a portion of the cyclohexylbenzene hydroperoxide contained in the oxidation product in the presence of an acid catalyst to produce a cleavage reaction mixture comprising the acid catalyst, phenol, and cyclohexanone. As used herein, "cleaving" means causing a cleavage reaction to occur. In the cleavage reaction, at least a portion of the desired cyclohexyl-1-phenyl-1-hydroperoxide desirably decomposes in high selectivity to cyclohexanone and phenol, and further, other hydroperoxides present may decompose to form various products, discussed below.

The acid catalyst may be at least partially soluble in the cleavage reaction mixture, stable at a temperature of at least 185° C. and has a lower volatility (higher normal boiling point) than cyclohexylbenzene.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

The cleavage reaction occurs under cleavage conditions. Suitable cleavage conditions include a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

The cleavage reaction mixture may contain the acid catalyst at a concentration in a range from Cac1 ppm to Cac2 ppm by weight of the total weight of the cleavage reaction mixture, where Cac1 and Cac2 can be, independently, 10, 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Particularly desirably, Cac1 is 50, and Cac2 is 200.

Conversion of any hydroperoxide, such as cyclohexyl-1-phenyl-1-hydroperoxide, and conveniently all cyclohexyl-1-phenyl-1-hydroperoxide and other hydroperoxides, may be very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide, and other hydroperoxides present in the at least a portion of the oxidation product undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone according to the following desired Reaction-3:

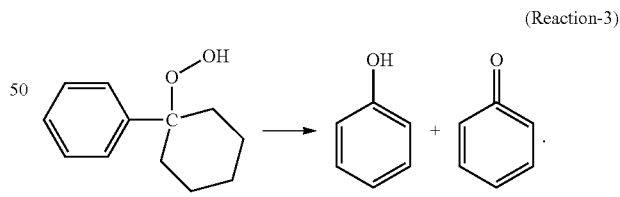

(Reaction-3)

Desirably, each mole of cyclohexyl-1-phenyl-1-hydroperoxide produces one mole of phenol and one mole of cyclohexanone. However, due to side reactions, the selectivity of the cleavage reaction of phenol can range from Sph1% to Sph2% and the selectivity of cyclohexanone can range from Sch1% to Sch2%, where Sph1, Sph2, Sch1, and Sch2 can be, independently, 85, 87, 88, 89, 90, 91, 92, 93, 94, 95, 96, 97, 98, 99, or even 99.5, as long as Sph1<Sph2, and Sch1<Sch2.

Besides the cleavage feed comprising cyclohexylbenzene hydroperoxide, cyclohexylbenzene and other components originating directly from the oxidation product, the cleavage reaction mixture may further comprise other added materials, such as the cleavage catalyst, a solvent, and one or more products of the cleavage reaction such as phenol and cyclohexanone recycled from the cleavage reaction effluent, or from a downstream separation step. Thus, the cleavage reaction mixture inside the cleavage reactor may comprise, based on the total weight of the cleavage reaction mixture: (i) phenol at a concentration from Cph1 wt % to Cph2 wt %, where Cph1 and Cph2 can be, independently, 20, 25, 30, 35, 40, 45, 50, 55, 60, 65, 70, 75, or 80, as long as Cph1<Cph2; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; (iii) cyclohexylbenzene at a concentration from Cchb1 wt % to Cchb2 wt %, where Cchb1 and Cchb2 can be, independently, 5, 8, 9, 10, 12, 14, 15, 18, 20, 22, 24, 25, 26, 28, 30, 35, 40, 45, 50, 55, 60, 65, 70, as long as Cchb1<Cchb2.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture, or the neutralized cleavage mixture, or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation product from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor comprises a plurality of reactors in series, each performing a portion of the conversion reaction, optionally operating in different modes and at different conditions selected to enhance the cleavage reaction at the pertinent conversion range. In one example, the cleavage reactor is a catalytic distillation unit.

The cleavage reactor may be operable to transport a portion of the contents through a cooling device and return the cooled portion to the cleavage reactor, thereby managing the exothermicity of the cleavage reaction. Alternatively, the reactor may be operated adiabatically. In one example, cooling coils operating within the cleavage reactor(s) remove any heat generated.

The cleavage reaction product exiting cleavage reactor may comprise, based on the total weight of the cleavage reaction mixture: (i) phenol at a concentration from Cph3 wt % to Cph4 wt %, where Cph1 and Cph2 can be, independently, 20, 25, 30, 35, 40, 45, 50, 55, 60, 65, 70, 75, or 80, as long as Cph3<Cph4; (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; (iii) cyclohexylbenzene at a concentration from Cchb3 wt % to Cchb4 wt %, where Cchb3 and Cchb4 can be, independently, 5, 8, 9, 10, 12, 14, 15, 18, 20, 22, 24, 25, 26, 28, 30, 35, 40, 45, 50, 55, 60, 65, 70, as long as Cchb3<Cchb4.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative to the cleavage reaction mixture as directly produced, may provide the at least a portion of the cleavage reaction mixture subjected to the neutralization reaction.

The cyclohexylbenzene contained in the cleavage reaction product can be separated from other major components, such as phenol and cyclohexanone by, e.g., distillation. The separated cyclohexylbenzene can then be treated and/or purified, e.g., by washing using an aqueous dispersion, before delivered to step (A) along with cyclohexylbenzene supplied from other resources, such as fresh cyclohexylbenzene produced the hydroalkylation reactor and a recycle cyclohexylbenzene stream from the cyclohexylbenzene hydroperoxide concentrator. Likewise, this recycle cyclohexylbenzene material, if washed with an aqueous dispersion, will be a source of the water contained in the reaction media in the oxidation reactor, and the water contained in the oxidation product.

Contaminant Treatment

As discussed above, the cleavage reaction mixture may comprise one or more contaminants. The processes may further comprise contacting at least a portion of a contaminant with an acidic material to convert at least a portion of the contaminant to a converted contaminant, thereby producing a modified reaction mixture. Detailed description of the contaminant treatment process can be found, e.g., in International Publication WO2012/036822A1, the relevant content of which is incorporated herein by reference in its entirety.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used, for example, to produce phenolic resins, bisphenol A, ε-caprolactam, adipic acid, and/or plasticizers.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

Non-limiting embodiments of the processes of the present disclosure include:

E1. A process for making phenol and/or cyclohexanone, the process comprising:

(A) oxidizing a cyclohexylbenzene feed to obtain an oxidation product comprising cyclohexylbenzene, cyclohexylbenzene hydroperoxide and water;

(B) removing at least a portion of the water from at least a portion of the oxidation product to obtain a cleavage feed; and (C) contacting at least a portion of the cyclohexylbenzene hydroperoxide in the cleavage feed with an acid catalyst in a cleavage reactor under cleavage conditions to obtain a cleavage product comprising phenol and cyclohexanone.

E2. The process of E1, wherein:
the oxidation product comprises water at a concentration of C1 ppm by weight;
the cleavage feed comprises water at a concentration of C2 ppm by weight; and C1/C2≥2.0.

E3. The process of E1 or E2, wherein in the oxidizing step (A), the cyclohexylbenzene feed comprises water at a concentration of at least 100 ppm by weight, based on the total weight of the cyclohexylbenzene feed.

E4. The process of any of E1 to E3, wherein at least a portion of the cyclohexylbenzene feed has been washed by an aqueous dispersion.

E5. The process of any of E1 to E4, wherein at least a portion of the oxidation product is washed by an aqueous dispersion after step (A) but before step (B).

E6. The process of any of E1 to E5, wherein the removing step (B) comprises:
(B1) flashing at least a portion of the oxidation product at an absolute pressure in a range from 2.5 kPa to 50.0 kPa.

E7. The process of E6, wherein in step (B1), the temperature of the oxidation product subjected to flashing is in a range from 70° C. to 120° C.

E8. The process of E6 or E7, wherein in step (B1), at least 95% of the water contained in the oxidation product subjected to flashing is removed, the percentage based on the total amount of water contained in the oxidation product subjected to flashing.

E9. The process of any of E1 to E5, wherein the removing step (B) comprises:
(B2) separating at least a portion of the cyclohexylbenzene from the oxidation product.

E10. The process of any of E1 to E5, wherein the removing step (B) comprises:
(B1) flashing at least a portion of the oxidation product at an absolute pressure in a range from 2.5 kPa to 50.0 kPa; and
(B2) separating at least a portion of the cyclohexylbenzene from at least a portion of the oxidation product subjected to flashing in step (B1).

E11. The process of E10, wherein at least a part of steps (B1) and at least a part of step (B2) are conducted in the same vessel.

E12. The process of E10, wherein step (B1) is conducted in a first vessel having an internal absolute pressure of at least 3.0 kPa, and step (B2) is conducted in a second vessel having an internal absolute pressure of at most 2.7 kPa downstream of the first vessel.

E13. The process of any of E9 to E12, wherein in step (B2), a falling film evaporator is used.

E14. The process of any of E9 to E13, wherein at least a portion of the cyclohexylbenzene separated in step (B2) is recycled to step (A).

E15. The process of any of E1 to E14, wherein in the removing step (B2), the temperature of the oxidation product is controlled at below 115° C.

E16. The process of any of E1 to E15, wherein the cyclohexylbenzene removed in step (B2) is washed by using an aqueous dispersion and subsequently recycled to step (A).

E17. The process of any of E1 to E16, wherein the oxidation product has a cyclohexylbenzene hydroperoxide concentration of at most 30 wt %, and the cleavage feed has a cyclohexylbenzene hydroperoxide concentration of at least 40 wt %.

E18. The process of any of E1 to E17, wherein the oxidizing step (A) comprises contacting cyclohexylbenzene with oxygen in the presence of an oxidation catalyst.

E19. The process of E18, wherein the oxidizing step (A) comprises passing a stream of oxygen-containing gas through an oxidation reaction mixture comprising cyclohexylbenzene.

E20. The process of any of E1 to E19, wherein in step (C), the acid catalyst is selected from sulfuric acid, hydrochloric acid, phosphoric acid, perchloric acid, and sulfonic acids.

E21. The process of E20, wherein the concentration of the acid catalyst in the cleavage reactor is in a range from 50 ppm to 5000 ppm of the total weight of the reaction medium present in the cleavage reactor.

E22. The process of any of E1 to E21, wherein in step (C), the acid catalyst is fed into the cleavage reactor in liquid form.

E23. The process of any of E1 to E19, wherein in step (C), the acid catalyst comprises at least one of:
(i) a molecular sieve; and
(ii) a mixed oxide comprising at least one of Ti, Zr, W, Mo, V, Cr, Mn, Fe, Cu, and Zn.

E24. The process of any of E1 to E23, wherein in step (C), the temperature in the cleavage reactor is controlled within a range from 30° C. to 100° C.

E25. The process of any of E1 to E24, wherein in step (C), the cleavage product comprises water at a concentration of not higher than 100 ppm by weight.

E26. The process of any of E1 to E25, wherein in step (C), the cleavage product comprises residual cyclohexylbenzene, and the process further comprises:
(D) separating at least a portion of the residual cyclohexylbenzene from the cleavage product; and
(E) recycling at least a portion of the residual cyclohexylbenzene separated in step (D) to step (A).

E27. The process of E26, wherein at least a portion of the residual cyclohexylbenzene obtained in step (D) is washed by an aqueous dispersion before the recycling step (E).

E28. The process of any of E1 to E27, wherein in step (A), an oxidation catalyst having a structure of formula (FC-I), (FC-II), or (FC-III) below is used:

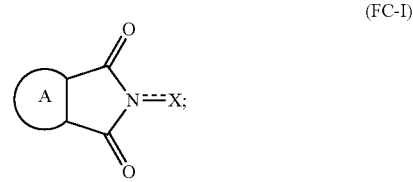

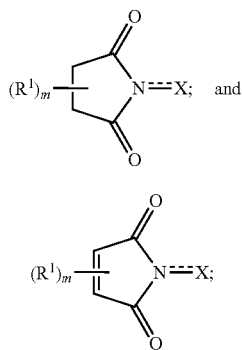

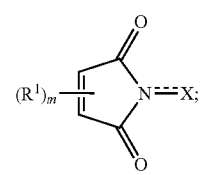

where:

A represents an optionally substituted ring;

X represents a hydrogen, an oxygen, a hydroxyl group, or a halogen;

$R^1$, the same or different at each occurrence, independently represents a halogen, a N-, S-, or O-containing group, or an optionally substituted linear or branched acyclic alkyl cyclic alkyl group having 1 to 20 carbon atoms; and m is 0, 1 or 2.

E29. The process of E28, wherein in step (A), an oxidation catalyst having a structure of formula (FC-IV) is used:

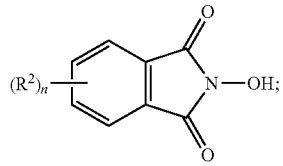

where:

$R^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

E30. The process of E28, wherein in step (A), N-hydroxyl phthalmic imide is used as an oxidation catalyst.

E31. The process of any of E28 to E30, wherein at least a portion of the oxidation catalyst is removed from the oxidation product before step (C).

The invention claimed is:

1. A process for making phenol and/or cyclohexanone, the process comprising:
 (A) oxidizing a cyclohexylbenzene feed to obtain an oxidation product comprising cyclohexylbenzene, cyclohexylbenzene hydroperoxide and water;
 (B) removing at least a portion of the water from at least a portion of the oxidation product to obtain a cleavage feed; and
 (C) contacting at least a portion of the cyclohexylbenzene hydroperoxide in the cleavage feed with an acid catalyst in a cleavage reactor under cleavage conditions to obtain a cleavage product comprising phenol and cyclohexanone,
 wherein the oxidation product comprises water at a concentration of C1 ppm by weight; the cleavage feed comprises water at a concentration of C2 ppm by weight; and C1/C2≥2.0.

2. The process of claim 1, wherein at least a portion of the cyclohexylbenzene feed has been washed by an aqueous dispersion.

3. The process of claim 1, wherein at least a portion of the oxidation product is washed by an aqueous dispersion after the oxidizing step (A) but before the removing step (B).

4. The process of claim 1, wherein the removing step (B) comprises:
 (B1) flashing at least a portion of the oxidation product at an absolute pressure in a range from 2.5 kPa to 50.0 kPa.

5. The process of claim 4, wherein in step (B1), the temperature of the oxidation product subjected to flashing is in a range from 70° C. to 120° C.

6. The process of claim 4, wherein in step (B1), at least 95% of the water contained in the oxidation product subjected to flashing is removed, the percentage based on the total amount of water contained in the oxidation product subjected to flashing.

7. The process of claim 1, wherein the removing step (B) comprises:
 (B2) separating at least a portion of the cyclohexylbenzene from the oxidation product.

8. The process of claim 1, wherein the removing step (B) comprises:
 (B1) flashing at least a portion of the oxidation product at an absolute pressure in a range from 2.5 kPa to 50.0 kPa; and
 (B2) separating at least a portion of the cyclohexylbenzene from at least a portion of the oxidation product subjected to flashing in the flashing step (B1).

9. The process of claim 8, wherein step (B1) is conducted in a first vessel having an internal absolute pressure of at least 3.0 kPa, and step (B2) is conducted in a second vessel having an internal absolute pressure of at most 2.7 kPa downstream of the first vessel.

10. The process of claim 7, wherein in the separating step (B2), at least one falling film evaporator is used.

11. The process of claim 7, wherein at least a portion of the cyclohexylbenzene separated in the flashing step (B2) is recycled to step (A).

12. The process of claim 7, wherein the cyclohexylbenzene removed in step (B2) is washed by using an aqueous dispersion and subsequently recycled to step (A).

13. The process of claim 1, wherein in step (C), the temperature in the cleavage reactor is controlled within a range from 30° C. to 100° C.

14. The process of claim 1, wherein in step (C), the cleavage product comprises residual cyclohexylbenzene, and the process further comprises:
 (D) separating at least a portion of the residual cyclohexylbenzene from the cleavage product; and
 (E) recycling at least a portion of the residual cyclohexylbenzene separated in step (D) to step (A).

15. The process of claim 14, wherein at least a portion of the residual cyclohexylbenzene obtained in step (D) is washed by an aqueous dispersion before the recycling step (E).

16. The process of claim 1, wherein in step (A), an oxidation catalyst having a structure of formula (FC-I), (FC-II), or (FC-III) below is used:

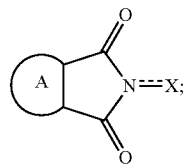
(FC-I)

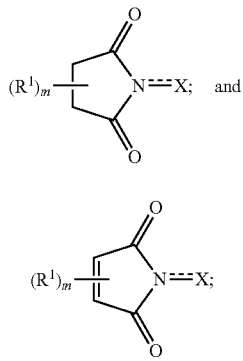
(FC-II)

(FC-III)

where:

A represents an optionally substituted ring;

X represents a hydrogen, an oxygen, a hydroxyl group, or a halogen;

$R^1$, the same or different at each occurrence, independently represents a halogen, a N-, S-, or O-containing group, or an optionally substituted linear or branched acyclic alkyl or cyclic alkyl group having 1 to 20 carbon atoms; and m is 0, 1 or 2.

17. The process of claim 16, wherein in step (A), an oxidation catalyst having a structure of formula (FC-IV) is used:

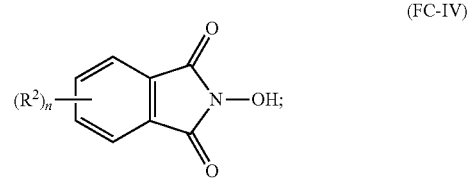
(FC-IV)

where:

$R^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

18. The process of claim 17, wherein in step (A), N-hydroxyl phthalmic imide is used as an oxidation catalyst.

19. The process of claim 17, wherein at least a portion of the oxidation catalyst is removed from the oxidation product before step (C).

20. The process of claim 1, wherein Cl ranges from 30 to 5000 ppm by weight.

* * * * *